United States Patent
Schiavo et al.

(12) 
(10) Patent No.: US 7,201,916 B2
(45) Date of Patent: Apr. 10, 2007

(54) LIQUID EMANATOR DEVICE TO DELIVER SELF-SUSPENDING INSECTICIDE DROPLETS

(75) Inventors: Glenn Schiavo, Campbell, CA (US); Dean Fanara, Twain Hearte, CA (US)

(73) Assignee: Henkel Consumer Goods Inc., Scottsdale, AZ (US)

( * ) Notice: Subject to any disclaimer, the term of this patent is extended or adjusted under 35 U.S.C. 154(b) by 746 days.

(21) Appl. No.: 09/870,117

(22) Filed: May 30, 2001

(65) Prior Publication Data

US 2002/0192255 A1 Dec. 19, 2002

(51) Int. Cl.
*A01N 25/08* (2006.01)
(52) U.S. Cl. .................. 424/409; 43/125; 43/129; 424/40; 424/43; 424/405
(58) Field of Classification Search ................ 424/405, 424/409, 43, 40; 43/125, 129
See application file for complete search history.

(56) References Cited

U.S. PATENT DOCUMENTS 4,532,530 A 7/1985 Hawkins
5,000,383 A * 3/1991 van der Heijden ............ 239/47
5,646,660 A 7/1997 Murray

FOREIGN PATENT DOCUMENTS

WO WO 00/51747 9/2000

OTHER PUBLICATIONS

Liquid Emantor Devices (Vaporistion Products), AgrEvo Environmental Health, 8 pages.

* cited by examiner

*Primary Examiner*—Neil S. Levy
(74) *Attorney, Agent, or Firm*—Ray K. Shahani; Paul A. Pappalardo

(57) ABSTRACT

A method and device for metered delivery of an insecticidal liquid into a room for the purpose of repelling or killing flying insects, wherein the liquid is ejected in small quantities from a bubble-jet type liquid emanator device at an ambient temperature. The ejected droplets may also be charged to $(-1 \times 10^{-4}$ C/Kg) by passing the droplets through a static field which will cause the droplets to be attracted to the positive charge which exists across the insects cuticle. Other applications include dispensation of fragrances and air fresheners into a room.

5 Claims, 9 Drawing Sheets

LIQUID EMANATOR DEVICE TO DELIVER SELF-SUSPENDING INSECTICIDE DROPLETS

RELATED INVENTIONS

This Application is related to and incorporates herein by reference, in its entirety, U.S. patent application Ser. No. 09/207,397 filed Dec. 8, 1998, entitled LIQUID EMANATOR DEVICE TO DELIVER SELF-SUSPENDING INSECTICIDE DROPLETS and claims any and all benefits to which it is entitled therefrom.

FIELD OF THE INVENTION

The invention relates to a method for the metered delivery of an insecticidal liquid into a room for the purpose of repelling or killing mosquitoes or other flying insects, where the liquid is ejected in small quantities from a bubble-jet type or equivalent liquid atomizing device. By passing the ejected droplets through a static field they can be imparted with a charge opposite that of the insects cuticle, attracting them to the insect.

BACKGROUND OF THE INVENTION

In tropically located countries, like those in South America and Asia, mosquitoes are more than a simple nuisance, they are vectors of deadly diseases. Diseases like Dengue Haemorrhagic fever, Malaria, Yellow Fever, and various types of Encephalitis. Protecting ones self and family from these diseases is a premium concern of individuals in these areas. Devices that repel and kill mosquitoes abound in these places. There are 3 basic types of anti-mosquito devices, aerosol insecticides, coils, and electrical devices like mats and emanators.

Aerosols dispense oil or water based, insecticide containing droplets into the air which impact on the mosquito, delivering the insecticide and killing the insect. These droplets impact on mosquitoes and either repel them or kill them depending upon how many droplets the mosquito encounters. Aerosols are effective from a few minutes to 2 hours.

Coils are composed of pressed sawdust impregnated with a small amount of insecticide. The coil is lit with a match and begins to smolder slowly. As it smolders, the heat evaporates the insecticide into the air as a vapor where it quickly cools and forms micron sized droplets 2–5 µm in size.

Electrical devices like mats and emanators use electrical heat instead of smoldering sawdust. Mats are insecticide and a carrier or solvent impregnated into cotton linter that are placed on a small metallic heating plate which drives off the active ingredient into the air in the same manner as the coils. Mats can last from 4–13 hours.

Emanators work much the same way but they use a liquid reservoir which contains insecticide and a carrier solvent. The insecticide is carried up to the heating element by a wick, usually ceramic. Because the reservoirs are large, emanators can last up to 90 days.

Electrically powered flying insect killers, like other emanator devices have been growing in popularity for some time. Emanators are preferred over aerosols because of the convenience of long operation and their odorless operation.

They are safer than coils, with their drastically reduced fire risk, and cleaner because there are no messy ashes or smoke to deal with. They cost less, in day to day usage, than mats or coils. They are more modern, upscale products, preferred over seemingly low-tech coils and aerosols.

But even the traditional emanator has its problems. Emanators require heat, drawing a fair amount of power and normally running at a dangerously high temperature. Burns are common with these products and there is always a risk of fire where there is excessive high heat. Emanators must be plugged into a wall socket, meaning placement is limited. Emanators must be operating at full temperature to drive off mosquitoes, and they usually take quite a while to heat up. Consumers may have to wait for an hour after turning on their device before seeing any mosquito reduction. Because of the heat involved, emanator devices often have problems with insecticide vapors condensing on the plastic casing, or walls immediately adjacent to the device. Because different insecticides evaporate off at different temperatures, the heater temperature, active ingredient evaporation temperature and solvent evaporation temperature must be precisely matched.

FIG. 1A is a representative perspective view of a liquid emanator device 100 of the prior art. FIG. 1B is a representative partial cutaway view of a liquid emanator device of the prior art. Liquid emanator devices 100 are the most recent stage in the evolution of products for vaporizing anti-mosquito and other insect formulations. Typically, these devices 100 comprise a reservoir 102 containing an insecticidal solution, formulation or compound 104. The insecticidal solution 104 is typically a hydrocarbon solvent mixture with a dissolved pyrethroid insecticide. A wick 106, generally made of a carbon or ceramic-based material, is inserted into the insecticidal solution 104 at a liquid end 108. The other, non-immersed end 110 of the wick 106 is positioned within a heater element 112, similar to those found in mat heaters, but usually annular in shape to surround the wick 106.

A housing 120 couples the assembly together. Electrical contacts 122 and switch means 124 provide a source of electrical energy to the resistive heating element 112. As the solvent and insecticide solution 104 is vaporized from the heated area, solution moves up the wick 106 by capillary action. The major advantage of this type of device over other vaporizers is that it does not produce any smoke compared to coils, and it lasts longer than one night, compared to typical coils and mats.

Liquid emanator devices 100 provide flexibility in the way the devices 100 are used over time. They can be used in continuous operation, only during the day, only during the night, or as needed. Overall duration varies typically between 30 to 60 nights, at up to 10 hours per night.

Another advantage of the liquid emanator devices 100 of the prior art is that they allow use by a consumer without any direct contact with the insecticidal solution 104. The use of a semi-clear plastic reservoir bottle 102 provides a visible indication of when the formulation is exhausted. The reservoir portion 102 can be replaceable, refillable, detachable or permanently or otherwise coupled to the system 100.

FIG. 1C is a representative section view of a resistive heating element-type emanator device 150 of the prior art. In this type of device 150, the cap portion 152 is filled with a liquid or other form of insecticidal solution 154. The cap portion 152 couples securely and directly to the high thermal conducting metal surface 156 covering the PTC-type heating element 158. Any of different plug 160 options are available, and a housing portion 162 retains the assembly together.

In operation, electrical current directed through the PTC-type heating element 158 causes an increase in surface temperature of the high thermal conducting metal surface 156. As this heat is transferred to the cap portion 152 containing the insecticidal compound 154, the compound 154 is evaporated and driven out of vents 164 in the housing 162. Metering means 166. Such as adjustable vent portions, flaps, cover plates, passive and/or dynamic heat sink, or height adjustment mechanism, serves to control the degree, amount, rate or other parameter of vaporization of insecticidal compound 154.

Atomization of liquids can be achieved in many ways. U.S. Pat. No. 4,532,530, issued Jul. 30, 1985 to Hawkins teaches a bubble-jet printing device. U.S. Pat. No. 5,646,660, issued Jul. 8, 1997 to Murray teaches a printer ink cartridge with drive logic integrated circuit. Generally speaking, ink jet printing systems can be divided into two types; viz, continuous stream and drop-on-demand. In continuous stream ink jet systems, ink is emitted in a continuous stream under pressure through at least one orifice or nozzle. The stream is perturbed, so that the stream breaks up into droplets at a fixed distance from the orifice. At the break-up point, the droplets are charged in accordance with digital data signals and passed through an electrostatic field which adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is to not formed or expelled unless it is to be placed on the recording medium.

Since drop-on-demand systems require no ink recovery, charging or deflection, the system is much simpler than the continuous stream type. There are two types of drop-on-demand ink jet systems. The major components of one type of drop-on demand system are an ink filled channel or passageway having a nozzle on one end and a piezoelectric transducer near the other end to produce pressure pulses. The relatively large size of the transducer prevents close spacing of the nozzles and physical limitations of the transducer result in low ink drop velocity. Low drop velocity seriously diminishes tolerances for drop velocity variation and directionality, thus impacting the systems ability to produce high quality copies. The drop-on-demand systems which use piezoelectric devices to expel the droplets also suffer the disadvantage of a slow printing speed.

The bubble jet concept is the other drop-on-demand system, and it is very powerful because it produces high velocity droplets and allows very close spacing of nozzles. The major components of the second type of drop-on-demand system are an ink filled channel having a nozzle on one end and a heat generating resistor near the nozzle.

As the name suggests, printing signals representing digital information originate an electric current pulse in a resistive layer within each ink passageway near the orifice or nozzle, causing the ink in the immediate vicinity to evaporate almost instantaneously and create a bubble. The ink at the orifice is forced out as a propelled droplet as the bubble expands. The process is ready to start all over again as soon as hydrodynamic motion of the ink stops. With the introduction of a droplet ejection system based upon thermally generated bubbles, commonly referred to as the "bubble jet" system, the drop-on-demand ink jet printers provide simpler, lower cost devices than their continuous steam counterparts and yet have substantially the same high speed printing capability.

OBJECTS AND ADVANTAGES

An object of the present invention is to provide a method or device for the delivery of insecticidal liquid into a room without utilizing traditional methods of heat.

It is a further object and advantage of the present invention to provide an ink-jet or bubble-jet type liquid atomizing device for the purpose The object is achieved in a method of utilizing the procedure in which a partial volume of liquid in a bubble-jet tube is evaporated and expanded for a short time in order to eject a quantity of the liquid through the jet to the atmosphere at room or ambient temperature.

The technology on which the method according to the invention is based is known from computer printers, where it is referred to as the ink-jet or bubble-jet technique. In the framework of the present invention, it has been established, surprisingly, that this printing technique can be transferred to the delivery of liquids, such as formulated insecticides, fragrances, air fresheners and the like into a room.

Bubble-jets can be adapted to deliver insecticidal solution with droplets as small as 8 picoliters. The bubble-jet emanator head of the present invention can be made up of up to hundreds of tiny tubes, each with a very small resistor near the tip. The bubble jet process starts with a pulsed signal (electrical current) in the resistors, which produces several thousand individual sudden temperature rises per second and each of these in turn forms a tiny bubble. This bubble exerts pressure and forces a single, ultra-fine droplet to be ejected at speeds up as high as or higher than 15 m/s. The pressure drops, a vacuum is created attracting new liquid, and the process begins all over again. The bubble-jet emanator heads of the present invention are capable of creating very fine droplets.

Bubble-jet printers already use alcohol and solvent based ink systems. Surprisingly, this matches very well with existing insecticidal formulation requirements.

The ambient emanator of the invention does not require heat. This eliminates the consumers risk of getting burned. It also drastically reduces the risk of fire, since it cannot heat up objects with which it comes in contact.

The ambient emanator can deliver precise dosages that can be instantaneously controlled with a control panel. It can be "turned up" to boost efficacy when flying insect activity is high or when attracting or offending odors are strong. It can then be turned down when flying insect activity or odor is low. By flying insects we mean any noxious or irritating insects, such as mosquitoes, gnats, flies and the like.

The common housefly, *Musca domestica*, occurs throughout the world in domestic situations. Along with similar species, such as the lesser housefly, blowflies and flesh flies, it contaminates food and spreads diseases, such as typhoid and cholera, and also carries the eggs of parasitic worms.

The mosquito is both a severe nuisance pest and vastly important as a vector for flood-borne diseases, such as malaria, yellow fever, dengue and the like.

Control of those insect pests is becoming more urgent as human populations increase and provide more resources for them to breed.

The ambient emanator may be portable. Evidence suggests that it may be possible to power the ambient emanator by batteries alone. The device would probably come with a plug, but it is possible for it to be battery powered and therefore, portable.

The ambient emanator needs no heat up time. Since the device would begin operating at full efficiency the moment it was turned on, there would be none of the warm up lag time associated with emanator devices. The ambient emanators time until mosquito reduction would depend on the diffusion time of the micron sized droplets, not the heating time of the element.

The ambient emanator would not cause condensation of the emitted vapor because the liquid would be emitted at room or ambient temperature.

The ambient emanator could use any active ingredient/formula because there is no temperature evaporation profile to match. Any active could be delivered into the air because there is no heat involved.

According to the present invention, in one aspect thereof there is provided a liquid delivery medium for use in a method in which the liquid delivery medium is ejected in droplet form from an orifice of a nozzle by the action of heat energy and the thus ejected liquid medium is ejected as small droplets into the atmosphere; the liquid medium comprising (a) an active agent which is a component to kill or repel flying insects, and (b) carrier liquid to dissolve or disperse the active agent in which a different T between a decomposition temperature of a substance having the lowest decomposition temperature among the substances constituting the active agent and a boiling point of the liquid delivery medium, exclusive of the active agent is at least 30° C.

According to the present invention, in another aspect thereof, there is provided a liquid delivery medium, wherein a gas in a quantity of 0.01 mL or more in terms of the conditions of 0° C. and 760 mm Hg is dissolved in 1 mL of the liquid medium at a normal ambient temperature, at which the liquid delivery medium is used.

As the droplets are ejected from the device, they can be passed through a static field, imparting them with a charge of ($-1 \times 10^{-4}$ Coulomb/Kg)—Method of Precipitating Airborne Particles, International Patent # WO 97/28883). This would cause the droplets to be attracted to the positive charge which exists across the insects cuticle (Beament, J. W. L. in *Nature Lond.* Vol. 191, pp217–221 from Pest Control, International Patent # WO 94/00980). By utilizing this method, more droplets will impinge on the insect through charge attraction than by chance alone, increasing the rate of kill.

For instance, these kinds of delivery methods should be excellent in signal response and faithfulness in reproduction, since the operation is done by ejecting droplets of the liquid medium from an orifice of a nozzle. Further, these methods are required to have various other characteristics such that the liquid medium can flow through the nozzle at a speed in conformity to the speed selected and that the liquid medium has long storage life, and various other factors. Furthermore, when electric or electrostatic method is adopted for the liquid ejecting method, or for controlling the sputtering direction of the droplets of the liquid medium, such electric or electrostatic characteristics are also taken into consideration to the above-mentioned properties. In order therefore to satisfy such various characteristics, those properties such as viscosity, surface tension, resistivity, electrical capacitance, dielectric constant, etc. of the liquid medium are properly regulated to desired values.

Thus, while the conventional liquid medium has been given various characteristics, they have been limited to the category of hydrodynamic and electrical characteristics in view of the nature of the modes, or, in view of the fact that the direct energy to eject and sputter the liquid medium from the orifice of the nozzle in the form of droplets is electrical or mechanical.

DETAILED DESCRIPTION OF THE PREFERRED EMBODIMENT

Figure 1A:
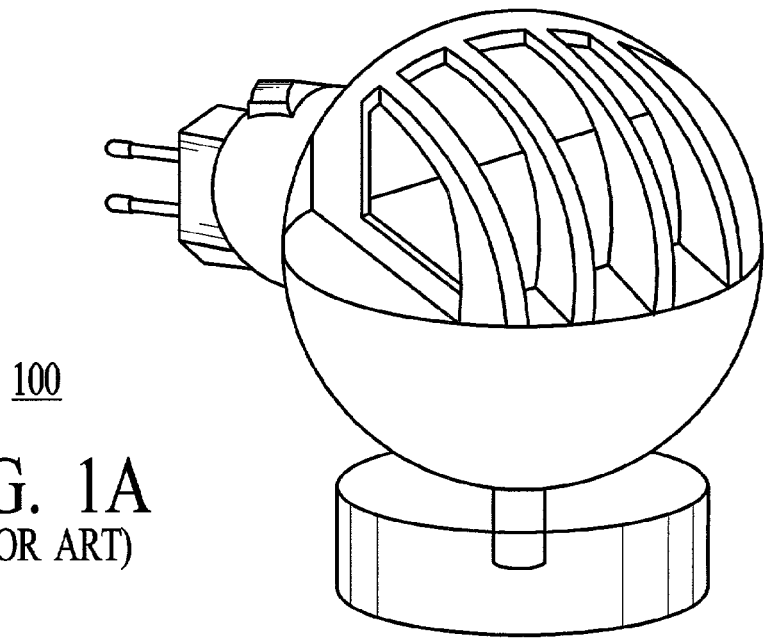
FIG. 1A is a representative perspective view of a liquid emanator device of the prior art.
Figure 1B:
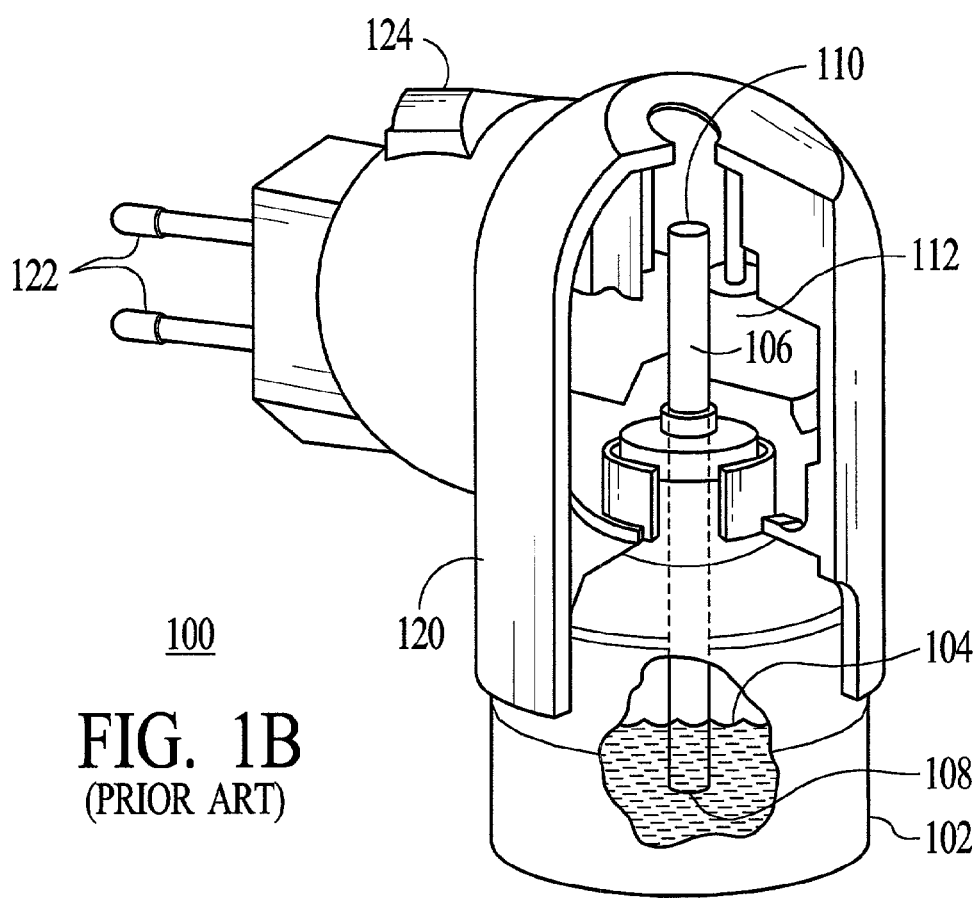
FIG. 1B is a representative partial cutaway view of a liquid emanator device of the prior art.
Figure 1C:
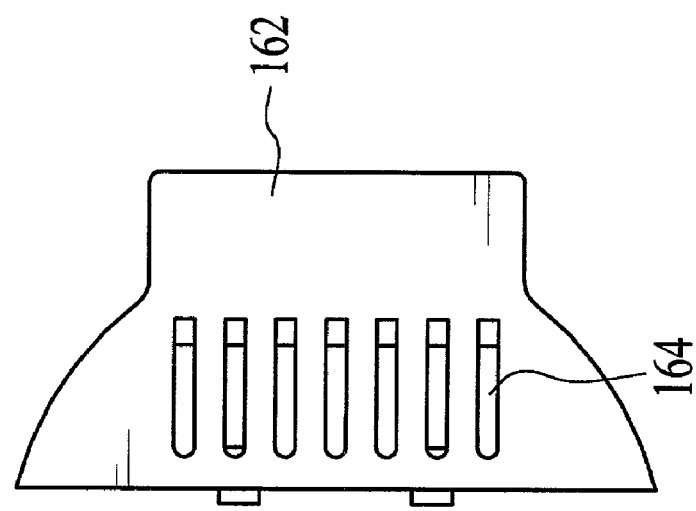
FIG. 1C is a representative section view of a resistive heating element-type liquid emanator device of the prior art.
Figure 1C:
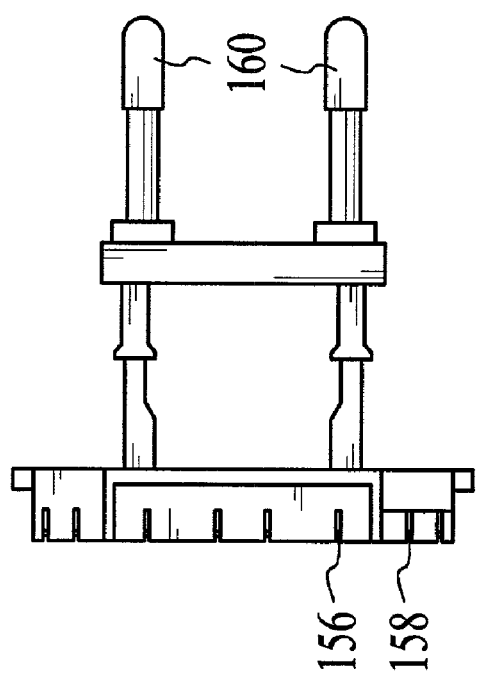
Figure 1C:
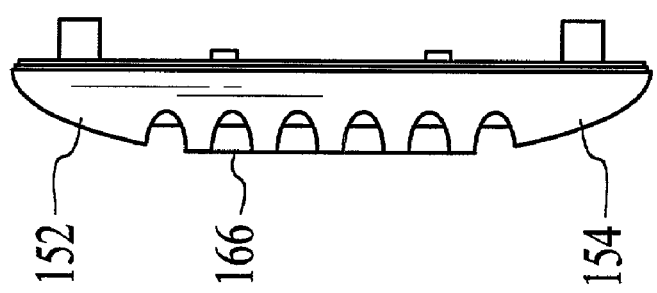

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

Liquid Insecticidal Formulation

The liquid delivery medium according to the present invention is composed of an active agent, a carrier liquid to dissolve or disperse the active agent, and additives to be added depending on necessity. These three components are properly selected and admixed in such a way that a difference between a decomposition temperature of the active agent and a boiling point of the liquid delivery medium except for the active agent may be 30° C. or higher.

The liquid delivery medium may also be prepared in such a way that a gas in an amount of 0.01 mL or more in terms of the condition of 0° C. and 760 mm Hg is dissolved in 1 mL of the liquid medium at a normal ambient temperature at which the liquid is used.

By "boiling point of the liquid medium except for the active agent" is meant the boiling point of the liquid medium, in case the liquid medium as prepared consists of an agent and a carrier liquid; and the boiling point of a composite system consisting of the carrier liquid and additives, but except for the agent, in case the liquid medium as prepared consists of the agent, the carrier liquid and the additives.

In a system containing a plurality of carrier liquid components, it is difficult, from time to time, to determine a single boiling point. In such case, the highest boiling point which any one of these carrier liquid components indicates may be used as the boiling point of the carrier liquid component.

By a "difference of 30° C. and higher between the decomposition temperature of the active agent and the boiling point of the liquid delivery medium except for the active agent" is meant the difference between the decomposition temperature of the active agent per se and the boiling point of the liquid delivery medium except for the active agent as defined above, when the delivery agent is of a single component system; and the difference between the decomposition temperature of a substance having the lowest decomposition temperature among those substances constituting the active agent and the boiling point of the liquid delivery medium as defined above, when the active agent is of a composite component system.

Further, by "normal ambient temperature when the liquid delivery medium is used" is meant an environmental temperature (including a temperature within a room), at which human beings generally live, i.e., a temperature range of from −10° C. to 50° C.

According to the present invention, there can be obtained such desirable liquid delivery medium which is remarkably small in consumption of heat energy necessary for the delivery, is extremely favorable in the heat response and stability in the droplet formation, is capable of coping with the delivery speed in its liquid feeding speed in the nozzle to a satisfactory extent, is free from lowering in the heat response and stability in the droplet formation with lapse of time, and does not bring about clogging of the nozzle at its heat energy applying section. Such liquid delivery medium can be realized by appropriately selecting and mixing the carrier liquid and the active agent, and, if necessary, adding the additives, in such a manner that the value of T may become 30° C. or higher, and, also, by positively dissolving a gas in the liquid delivery medium in an amount more than a determined quantity as calculated in terms of the dissolved quantity of such gas when converted to 0° C.

Therefore, by the use of the liquid delivery medium of the present invention, stable delivery operation can always be attained with a low energy consumption, and the resulting delivery into a room is high, is sufficient and is free from excessively large spray droplets.

An extremely favorable result can be obtained, in particular, when the temperature difference between the decomposition temperature of the agent and the boiling point of the liquid delivery medium component except for the active agent is set at 30° C. or higher, preferably 40° C. or higher, or optimally 50° C. or higher, and the dissolved quantity of a gas in the liquid delivery medium at a normal ambient temperature is 0.01 mL/mL or higher.

The delivery liquid for use in the present invention is for dissolving or dispersing the active agent. Various sorts of "solvents" available in the general market can be effectively used for this purpose.

Such delivery liquid can be broadly classified into an aqueous type solvent and a non-aqueous type solvent. Examples of such non-aqueous solvent are alkylalcohols having 1 to 10 carbon atoms such as methyl alcohol, ethyl alcohol, n-propyl alcohol, isopropyl alcohol, n-butyl alcohol, sec-butyl alcohol, tert-butyl alcohol, isobutyl alcohol, amyl alcohol, hexyl alcohol, heptyl alcohol, octyl alcohol, nonylalcohol, decyl alcohol, etc.; hydrocarbon solvents such as hexane, octane, cyclopentane, benzene, toluene, xylol, etc.; halogenated hydrocarbon solvents such as carbon tetrachloride, trichloroethylene, tetrachloroethane, dichlorobenzene, etc.; ether solvents such as ethylether, butylether, ethylene glycol diethylether, ethylene glycol monoethylether, etc.; ketone solvents such as acetone, methylethylketone, methylpropylketone, methylamylketone, cyclohexane, etc.; ester solvents such as ethyl formate, methyl acetate, propyl acetate, phenyl acetate, ethylene glycol monoethylether acetate; etc.; alcohol solvents such as diacetone alcohol, etc.; and high-boiling hydrocarbon solvents.

The above-mentioned delivery liquids are suitably selected in consideration of their affinity for the active agent and other additives to be added depending on necessity, and, in order to satisfy the foregoing requirements, they may be used as a mixture of two or more kinds, or a mixture with water, if necessary, within such a limit that a desirable delivery medium is obtainable.

Among the carrier liquids mentioned above, preferred are lower alcohols, water or water soluble solvents, especially water-alcohol mixtures in consideration of ecology, availability and easier preparation.

For one or a combination of gases to be dissolved in the liquid delivery medium according to the present invention, any kinds of gases that do not cause mal effect such as yielding of precipitation in the liquid delivery medium, bringing about undesirable chemical reaction with other components constituting the liquid delivery medium and active agent and being harmful to human bodies, can be suitably used.

Concrete examples of such gases are: hydrogen, nitrogen, oxygen, air, helium, neon, argon, krypton, xenon, methane, ethane, ethylene, acetylene, and so on. These gases may also be used in proper mixture among them depending on necessity. Of these gases, $N_2$, $CO_2$, $O_2$ and air can be preferably adopted for the purpose of the present invention from an economical standpoint.

The quantity of the gas to be dissolved in the liquid delivery medium according to the present invention is so determined that the liquid delivery medium having desired characteristics may be obtained. A physical value of the dissolving quantity of the gas to satisfy this condition should desirably be 0.01 mL or above per 1 mL of the liquid delivery medium, or, usually, 0.0132 mL or above, when the dissolved quantity of the gas in a usual ambient temperature regions including, for example, room temperature, is converted to the conditions of 0° C. and 760 mm Hg.

Dissolution of the gas in a predetermined quantity into the liquid delivery medium can be effected by blowing the gas into the liquid delivery medium or blowing the same into the liquid medium which has previously been cooled.

The liquid delivery medium for use in the present invention is essentially composed of the delivery liquid and the active agent as explained in the foregoing, but it may further contain other additive materials for realizing or improving the aforementioned characteristics required for the activity and delivery of the liquid or droplets.

Such additive materials include surfactants, solvents, viscosity regulating agents, surface tension regulating agents, pH regulating agents, resistivity regulating agents, wetting agents, infrared-absorbing heat-generating agents, etc.

Such viscosity regulating agent and surface tension regulating agent are added principally for attaining sufficient fluidity in the nozzle to keep up with the delivery speed, for preventing dropping of delivery medium and activity from the orifice of nozzle to the external surface thereof, and for blotting (expansions of spot as sputtered) on the active medium.

For these purposes, any known viscosity regulating agent or surface tension regulating agent is applicable as long as it does not provide undesirable effect to the delivery liquid and active agent.

Examples of such viscosity regulating agents are polyvinyl alcohol, hydroxypropyl cellulose, carboxymethyl cellulose, hydroxyethyl cellulose, methyl cellulose, water-soluble acrylic resins, polyvinyl pyrrolidone, gum arabic, starch, etc.

The surface tension regulating agents effective usable in the present invention include anionic, cationic and nonionic surface active agents, such as polyethylene glycolether sulfate, ester salt, etc, as the anionic compound; poly-2-vinylpyridine derivatives, poly4-vinylpyridine derivatives, etc. as the cationic compound; and polyoxyethylene alkylether, polyoxyethylene alkylphenylether polyoxyethylene alkyl esters, polyoxyethylene sorbitan alkylester, polyoxyethylene alkylamines, etc. as the nonionic compound. In addition to the above-mentioned surface active agents, there can be effectively employed other materials such as amine acids such as diethanolamine, propanolamine, morphole, etc., basic compounds such as ammonium hydroxide, sodium hydroxide, etc., and substituted pyrrolidones such as N-methyl-2-pyrrolidone, etc.

These surface tension regulating agents may also be employed as a mixture of two or more compounds so as to obtain a desired surface tension in the prepared liquid delivery medium and within a limit that they do not undesirably affect each other or affect other constituents.

The amount of the surface tension regulating agent is determined suitably according to the kind thereof, kind of other constituents, and desired activity characteristics. It is generally selected, with respect to 1 part by weight of delivery medium, in a range of from 0.0001 to 0.1 parts by weight, and preferably from 0.001 to 0.01 parts by weight.

Optionally, the pH regulating agent is added in a suitable amount to achieve a determined pH value, thereby improving the chemical stability of prepared liquid delivery medium, and avoiding changes in the physical properties of the medium as well as sedimentation or coagulation of the delivery agent or other components therein during a prolonged storage.

As the pH regulating agent adapted for use in the present invention, there can be employed almost any kind of materials capable of achieving a desired pH value without giving undesirable effects to the prepared liquid delivery medium.

Examples of such pH regulating agents are lower alkanolamine monovalent hydroxides such as alkali metal hydroxide, ammonium hydroxide, etc.

Such pH regulating agent is added in an amount required for realizing a desired pH value in the prepared delivery medium.

In case the delivery is conducted by electrically charging the droplets of the liquid delivery medium, the resistivity thereof is an important factor for determining the charging characteristics. In order that the droplets can be charged for a satisfactory delivery, the liquid delivery medium should have a resistivity generally within a range of $10^{-3}$ to $10^{11}$.

Examples of resistivity regulating agent to be added in a suitable amount to achieve the resistivity as explained above in the liquid delivery medium are inorganic salts such as ammonium chloride, sodium chloride, potassium chloride, etc., and quaternary ammonium salts.

In the delivery system wherein the droplets are not electrically charged, resistivity of the delivery medium need not be controlled.

As the wetting agent adapted for use in the present invention, there can be employed various materials known in the technical field related to the present invention, among which preferred are those thermally stable. Examples of such wetting agents are polyalkylene glycols such as polyethylene glycol, polypropylene glycol, etc.; alkylene glycols containing 2 to 6 carbon atoms such as ethylene glycol, propylene glycol, butylene glycol, hexylene glycol, etc.; lower alkyl ethers of diethylene glycol such as ethylene glycol methylether, diethylene glycol methylether, diethylene glycol ethylether, etc.; glycerin; lower alkoxy triglycols such as methoxy triglycol, ethoxy triglycol, etc.; N-vinyl-2-pyrrolidone oligomers, and the like.

Such wetting agents are added in an amount required for achieving desired properties in the delivery medium, and is generally added within a range of from 0.1 to 10 wt. %, preferably 0.1 to 8 wt. %, and most preferably 0.2 to 7 wt. %, with respect to the total weight of the liquid delivery medium. The above-mentioned wetting agents may be used, in addition to their individual use, as a mixture of two or more of them as long as they do not undesirably affect each other.

In a preferred embodiment, the insecticidal liquid delivery medium composition contains BHT, the common anti-oxidant and chemical additive 4-methyl-2-di-tert-butylphenol, also referred to as 2,6-di-tert-butyl-4-cresol, or butylated hydroxy toluene.

In a preferred embodiment, the insecticidal liquid delivery medium composition contains ISOPAR G. ISOPAR G is a solvent and solubilizing agent manufactured by the Exxon Company, consisting of approximately 100% heavy, hydrotreated petroleum naptha, predominantly $C_{10}$–$C_{11}$ isoparaffinic hydrocarbons, CAS no. 64742-48-9, which is useful for dissolving and delivering the active ingredient.

Active Agent

The active agent is selected in relation to the above-mentioned carrier liquid and to the additive materials so as to prevent sedimentation or coagulation in the nozzles and reservoir as well as clogging of pipes and orifices after prolonged standing. In the present invention, therefore, preferred is the use of active agents soluble in the carrier liquid, although those active agents which are difficult to solve in the delivery liquid are also usable for the purpose of the present invention so far as the size of dispersed particles is sufficiently small.

A wide range of insecticides may be included in the oil phase as required. These include natural pyrethrum and synthetic pyrethroids like prallethrin or s-bioallethrin. In addition, synergists such as MGK-264 or piperonyl butoxide may be included for use in conjunction with pyrethroid insecticides.

In a preferred embodiment, the active agent can be selected from any suitable insecticide or pesticide which has a decomposition temperature at least about 30° C. higher than the boiling point of the insecticidal liquid delivery medium. In a preferred embodiment, the active agent is ETOC-TG, also known as ETOC, the trade name for (+)-2-methyl4-oxo-3-(2-propynyl)-2-cyclopentenyl (+)-cis/ trans-chrysanthemate. ETOC-TG is an insecticide with common name "prallethrin", produced by Sumitomo Chemical Co., Ltd. ETOC-TG has a boiling point (BP) of 596° F., while decomposition of the chemical occurs above 608° F. Another insecticidal active agent which can be used in the present invention is transfluthrin which has a BP of 275° F., while decomposition occurs above 392° F.

The active agent to be employed in the present invention is to be suitably selected according to the desired result or effect and other delivery conditions to be used in the delivery.

Delivery System

The present invention incorporates U.S. Pat. Nos. 4,532,530, and 5,646,660 in their entirety. The major components of a first embodiment of the present invention are an insecticidal liquid filled channel or passageway having a nozzle on one end and a piezoelectric transducer near the other end to produce pressure pulses. The drawbacks associated with the use of piezo-electric transducers for printers is not necessarily a concern in the present application. The systems of the present invention use piezoelectric devices to expel the droplets as in printer devices.

The bubble jet concept is the other embodiment of the present invention. It produces high velocity droplets and allows very close spacing of nozzles. The major components of this embodiment of liquid atomizing device are an insecticidal liquid filled channel having a nozzle on one end and a heat generating resistor near the nozzle. An electric current pulse in a resistive layer within each insecticidal liquid passageway near the orifice or nozzle, causing the insecticidal liquid in the immediate vicinity to evaporate almost instantaneously and create a bubble. The insecticidal liquid at the orifice is forced out as a propelled droplet as the bubble expands. The process is ready to start all over again as soon as hydrodynamic motion of the insecticidal liquid stops.

Through the use of bubble-jet or piezojets to deliver microscopic droplets of solution containing active ingredient into the air. Any common or typical bubble-jets such as those which deliver ink can be used. The bubble-jet delivery head of the present invention is made up of anywhere between 1 to 10 to up to hundreds of tiny tubes, each with a very small resistor near the tip. These resistors are any resistive heating means. The bubble jet process of the present invention starts with an electrical pulse or other signal in the resistors, which produces a sudden temperature rise in the resistor on the tip portion of each tiny tube, and each of these in turn forms a tiny bubble. This bubble exerts pressure and forces a single, ultra-fine droplet to be ejected at 15 m/s, or more or less. The pressure drops, a vacuum is created attracting new liquid, and the process begins all over again. The bubble-jet or other delivery heads of the emanator system of the present invention are capable of creating very fine droplets. The droplets sizes can be reduced even further by using fast evaporating organic solvents, such as the type used in the present invention, or similarly fast evaporating cosolvent, to the liquid carrier. Thus, the liquid delivery medium droplets rapidly evaporate down to a very small droplet size which hangs in the air for extended periods of time.

Figure 2A:
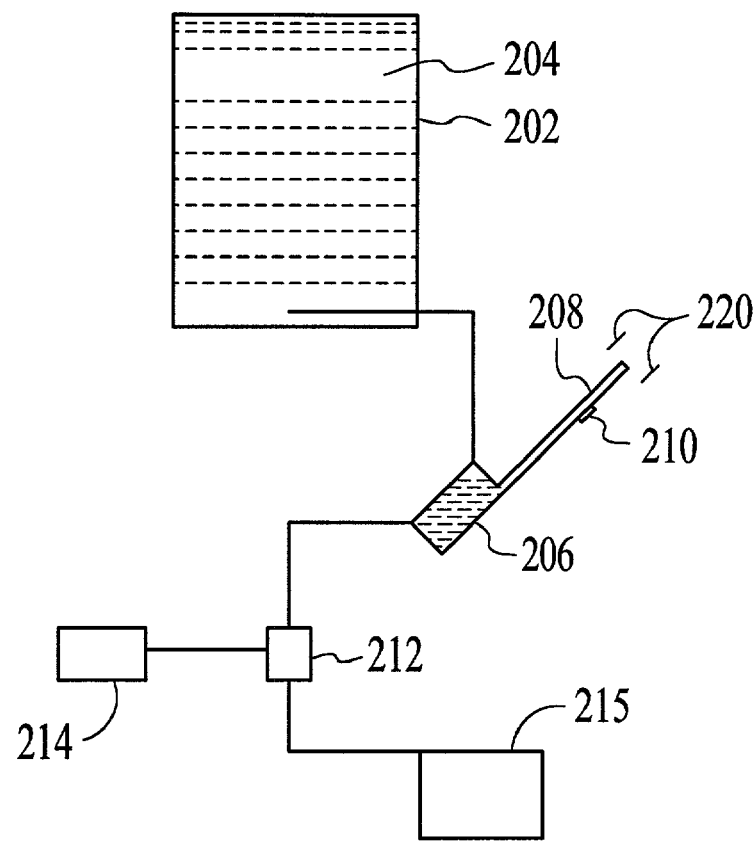
FIG. 2A is a block diagram-type schematic view of a preferred embodiment of the bubble-jet type liquid emanator device of the present invent

FIG. 2A is a block diagram-type schematic view of a preferred embodiment of the bubble-jet type liquid emanator device 200 of the present invention. This drawing shows how liquid insecticidal formulations can be delivered into a room at ambient temperature. The term "room" generally denotes a standard room in a home about 12 m³. A disposable and/or refillable cartridge or reservoir 202 contains an insecticidal formulation liquid 204. The liquid 204 feeds by gravity into a secondary reservoir 206 that holds liquid 204 ready to be dispensed therefrom. The liquid 204 feeds from the secondary reservoir 206 into one or more individual bubble-jet tubes 208. A resistive heating element 210 is in contact with the bubble jet tube(s) 208. The resistive heating element 210 is controlled by a control unit 212. According to fixed or adjustable settings on a control panel 214, the control unit 212, powered by a power unit 216, sends electrical impulses to the resistive heating element 210 every time a quantity of insecticidal liquid 204 is to be delivered.

In the present invention, each of the individual bubble-jet tubes 208 deliver insecticidal fluid 204 at various rates, with fluid 204 droplets as small as or smaller than 8 picoliters. This bubble exerts pressure and forces a single, ultra-fine droplet to be ejected at speeds up to or greater than 15 m/s. Upon formation and ejection from the tube 208, the pressure drops within the tube 208, and a (capillary) vacuum is created attracting new liquid, and the process begins all over again. The bubble-jet emanator heads of the devices 200 of the present invention are capable of creating very fine droplets.

As the vapor bubble is ejected it can be made to pass through a static field generated by a static field generator 220, which would impart the droplets with a charge of about $(-1 \times 10^{-4}$ C/Kg), or more or less, causing them to be attracted to the positive charge across the insects cuticle. If the liquid formula 204 itself were imparted with a negative charge then the static field generator 220 would also serve as a particle accelerator. The solvent phase of the insecticide containing droplet rapidly evaporates to an overall droplet volume medium diameter (VMD) of from about 1 µm to about 7 µm, or more or less. These droplets are effectively self supporting in the air.

(A droplet size of 5 µm will remain airborne in a completely stagnant room for nearly 20 minutes, while a 1 µm droplet will remain airborne for 18 hours. The *Aerosol Handbook*, Montfort A. Johnsen, 1982, states that, "because of lateral wind currents, the falling rate of particles below 5 µm in mean diameter may have little pragmatic meaning". These small insecticide filled droplets hang in the room and impinge on insects passing through the air causing them to be repelled if the impinged dosage is low and killed if it is high.

In addition to the conditions of T (a temperature difference between the decomposition temperature of the active agent and the boiling point of the liquid delivery medium exclusive of the recording agent) and the quantity of dissolved gas to provide the liquid medium with the above-mentioned various characteristics, preferably the liquid delivery medium 204 of the present invention is so prepared that the values of the following physical properties may be within a specific conditional range: for example, specific heat, thermal expansion coefficient, thermal conductivity, viscosity, surface tension, pH, and resistivity when the delivery is performed using droplets of electrically charged liquid delivery medium 204. In other words, these various physical properties play an important role on the characteristics of the liquid delivery medium 204 to be defined by and the dissolved quantity of gas such as, for example, stability in droplet-forming phenomenon, response and fidelity to the effect of thermal energy, chemical stability, fluidity in the nozzle, and so forth. Accordingly, these physical properties of the liquid 204 should preferably be taken into consideration when preparing the liquid delivery medium 204 according to the present invention.

When the electrical energy, for example, is used, there may be adopted various methods such as providing a heat conversion member such as the so-called thermal head or Peltier element, etc. on the tube portion 208 either directly or indirectly.

The size of the droplets depends on the quantity of the liquid delivery medium present in the sector from the position of the electric heat conversion member to the nozzle (or orifice), physical parameters of the liquid delivery medium, magnitude of pulse signal, and so forth.

When the droplets of the liquid delivery medium are ejected from the tube 208 of the bubble jet, a quantity of the liquid delivery medium corresponding to the droplets as ejected therethrough is replenished form the liquid feeding section, whereby the tube 208 interior reinstates its original, thermally standing state until a subsequent pulse signal is applied to the heat applying section of the tube 208. It should be noted that the feeding time of the liquid delivery medium be shorter than the on-off period of the pulse signal to be applied.

Droplets ejected from the ambient emanator of this invention would have an initial droplet size of 21 µm and a weight of 8 ng. The ideal emanator delivery dosage is 20 mg/hour. With 3 bubble-jet emitters operating, one would need each jet firing at 231 Hz.

The control panel contains, optionally, an on/off switch as well as a rate controller with a normal and a high setting. The normal setting is normal 20 mg/hr delivery rate and the high rate can be 1.5 to 2.0 times higher. In a preferred embodiment of the control scheme adapted for the system of the present invention, the high setting is timed to last a maximum of 1 hour before reverting to the normal setting. Alternate and preferred embodiments of the control scheme will be those associated with the prior art, and will be expressly and inherently incorporated herein by reference in their entireties.

Figure 2B:
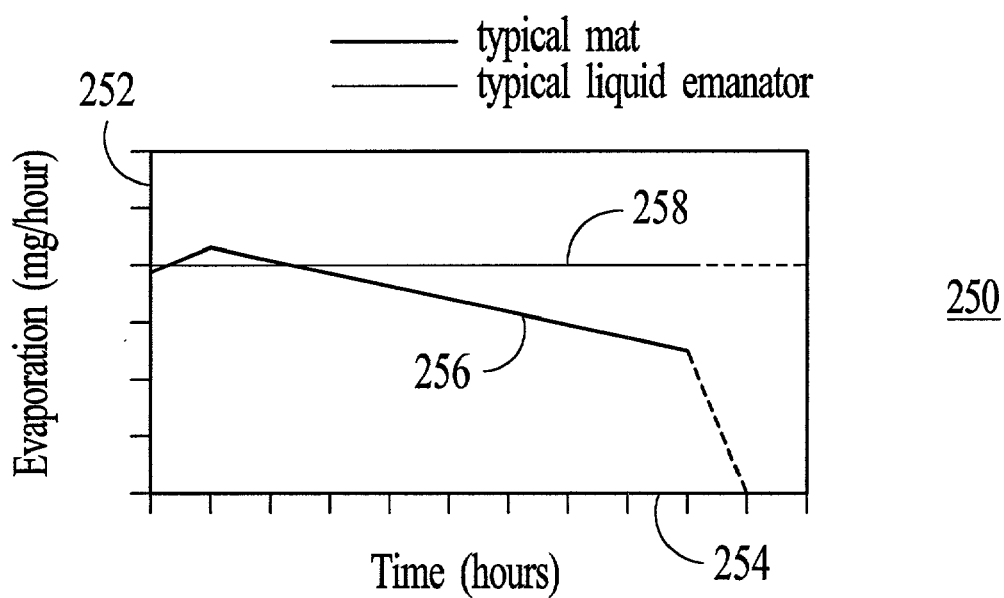
FIG. 2B is a comparison of vaporization between prior art and the present invention.

FIG. 2B is a comparison of vaporization rates between devices and methods of the prior art and the present invention. As shown, the drawing is a plot 250 of evaporation rate 252, in milligrams/hour, versus time 254, in hours. The line showing performance rate versus time for prior art devices 256 can be seen to increase generally for a brief time to a high or excessively high range, and then it begins a steady decline in effectivity. In comparison, the line showing the performance rate of the present invention versus time 258 can be seen to be steady, solid, essentially un-changing over time. This constant, linear, steady-state delivery rate is a valuable improvement over the prior art.

Figure 3A:
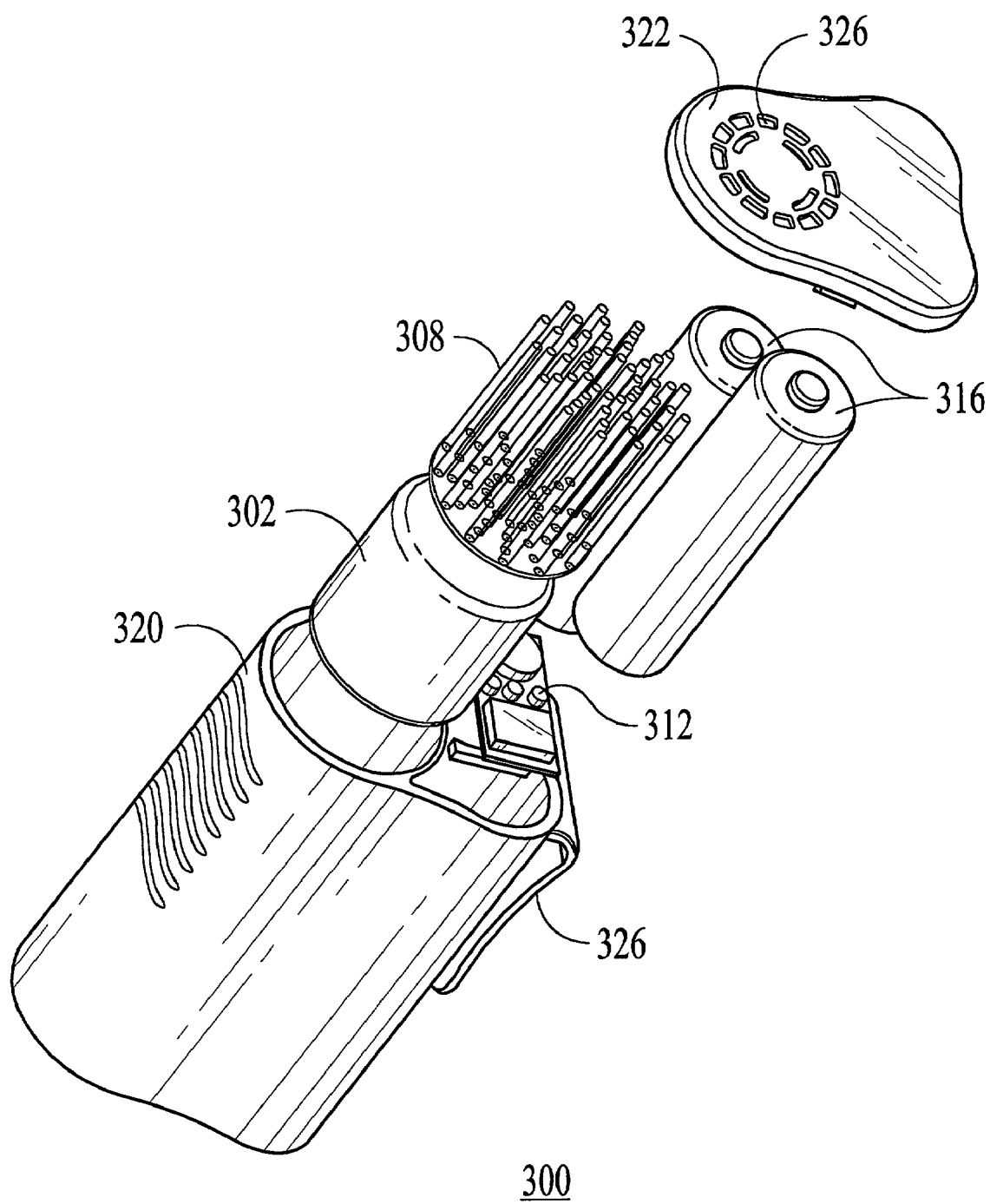
FIG. 3A is a representative isometric exploded view of a preferred embodiment of the portable emanator device of the present invention.

FIG. 3A is a representative isometric exploded view of a preferred embodiment of the portable emanator device 300 of the present invention. It will be understood that the design of the device 300 can be modified as needed or desired, and that the scope of the present invention includes all of those modifications. Fluid reservoir 302 communicates the insecticidal fluid 204 to the bubble jet tubes 308 upon delivery of electrical energy from battery pack 316 to the individual resistive heating elements (not shown), optionally controlled by controller 312.

Housing portion 320 and cap member 322 contain the reservoir portion 302, the battery pack 316, the controllers 312 and the bubble jet tubes 308. Vent holes 324 serve to allow the emanating insecticidal solution 204 out of the housing 320.

Optionally, the device 300 comprises means for coupling 326 the device 300 to a personal user, including a belt clip, other form of clip, velcro strap, other strap means, mounting bracket, etc. This feature allows a user to transport the device 300 as needed. It can also be mounted permanently or removably in one or more locations.

As described above, in preferred embodiments, the principle replacement components include the reservoir means 302 and the battery pack 316. These components can be provided individually or as a unit. Other replaceable components can include, optionally, the bubble jet tubes 308, etc. additionally, the reservoir means 302 can be replaceable or refillable. Likewise, the battery pack 316 or other power supply can be rechargeable or replaceable.

Figure 3B:
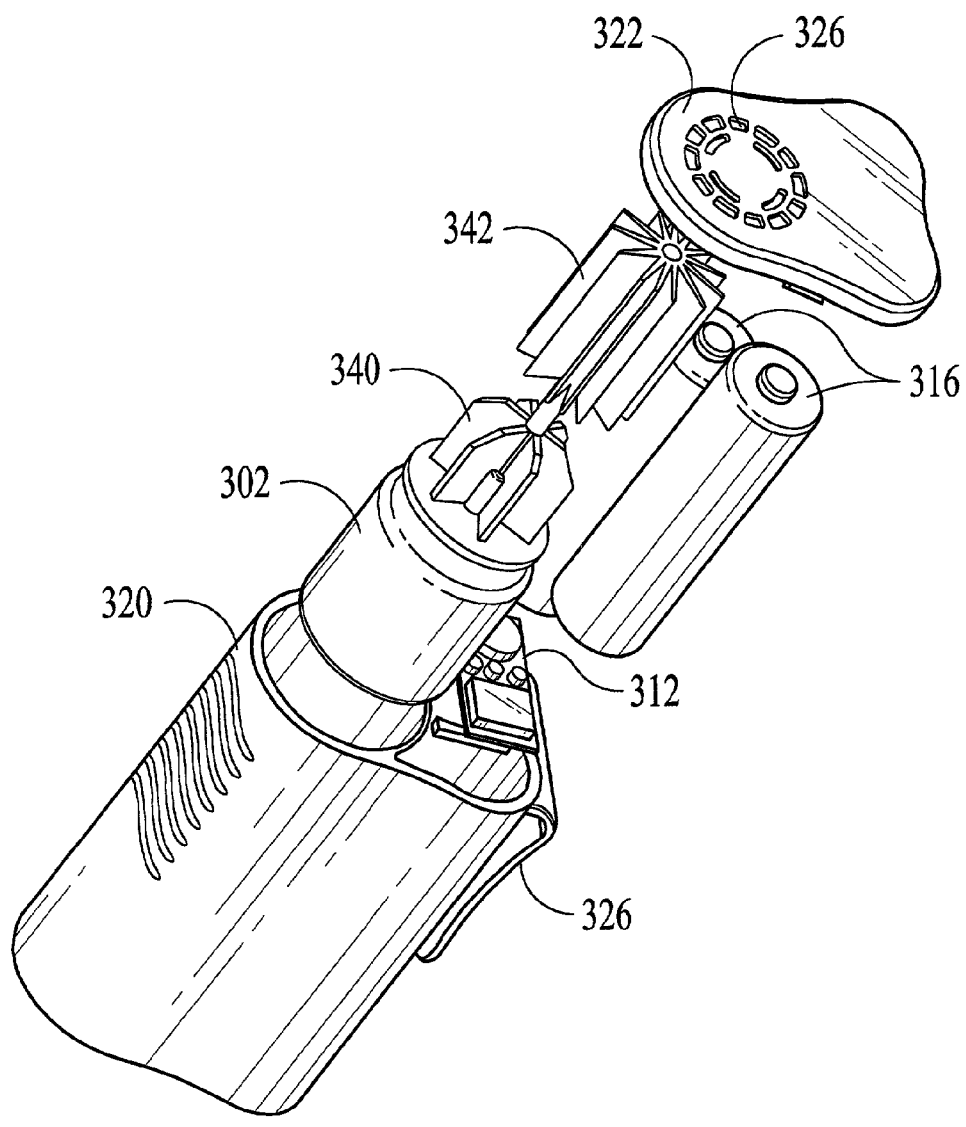
FIG. 3B is a representative isometric exploded view of another preferred embodiment of a portable emanator device of the present invention.

FIG. 3B is a representative isometric exploded view of another preferred embodiment of a portable emanator device 300B of the present invention. In this embodiment, the reservoir portion 302 and battery pack 316 or other power supply are similar to the embodiment shown in FIG. 3A. Furthermore, coupled to the bubble jet portion 340 there is a rotary delivery portion 342 which further serves to disperse the droplets of liquid insecticidal liquid 204 which emanate forth from the bubble jet portion 340 of the device 300B. This rotary delivery portion 342 acts as a fan to dispense the droplets. It can also comprise means 220 for applying a static charge to the droplets, as best shown in FIG. 2A.

Figure 4A:
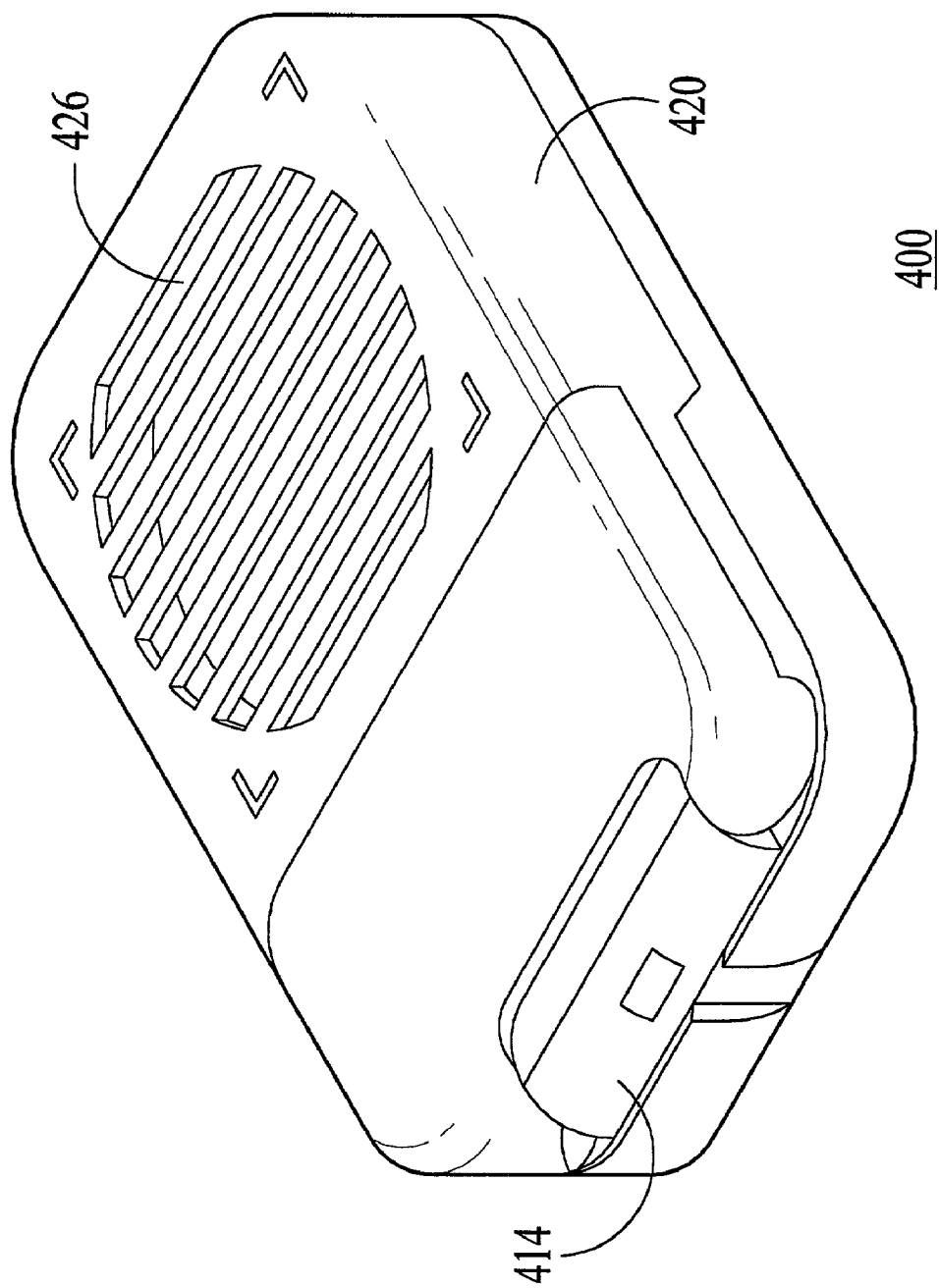
FIG. 4A is a representative isometric view of a preferred embodiment of a lower portion of a portable emanator device of the present invention.
Figure 4B:
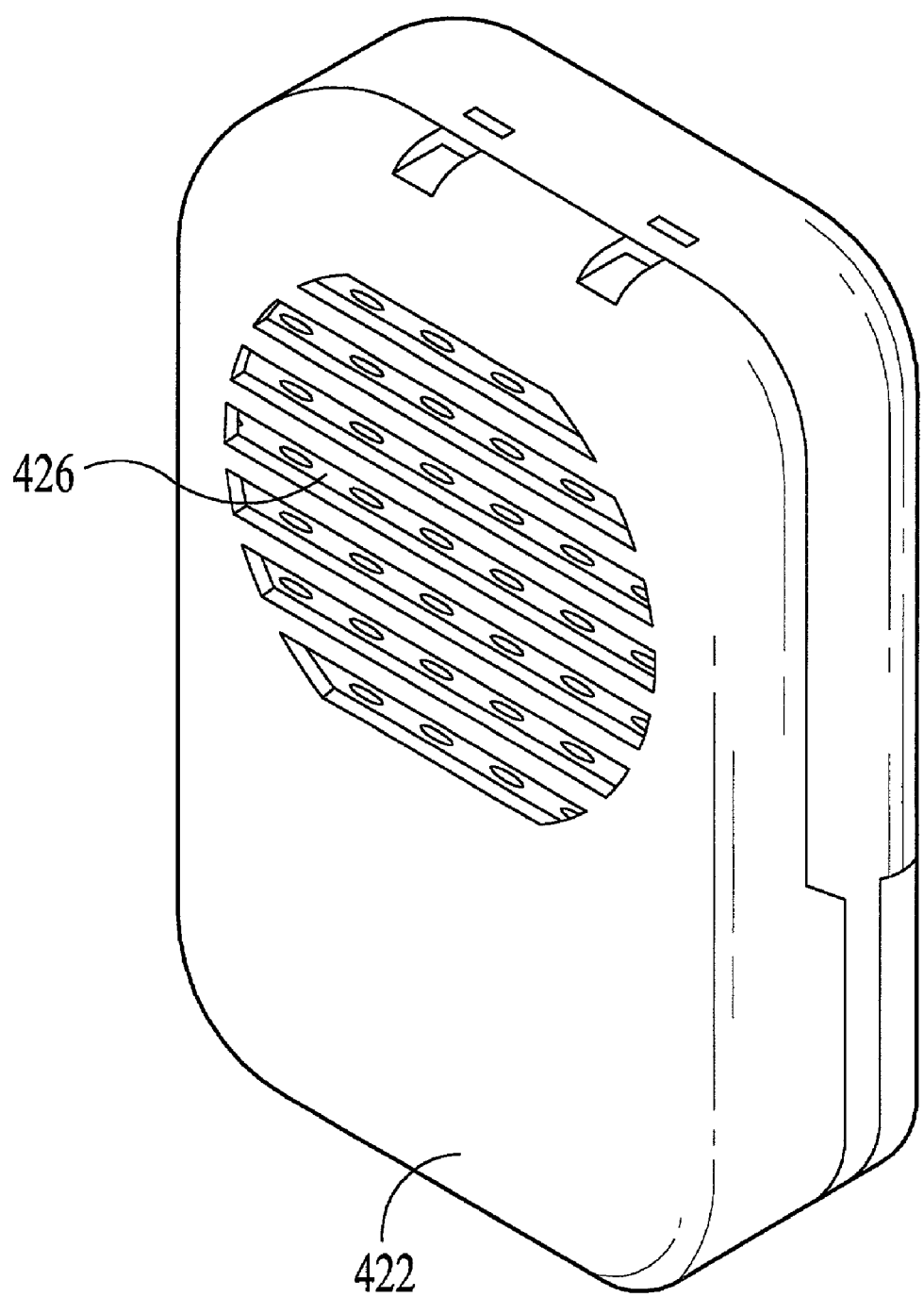
FIG. 4B is a representative isometric view of a preferred embodiment of an upper portion of a portable emanator device of the present invention.
Figure 4C:
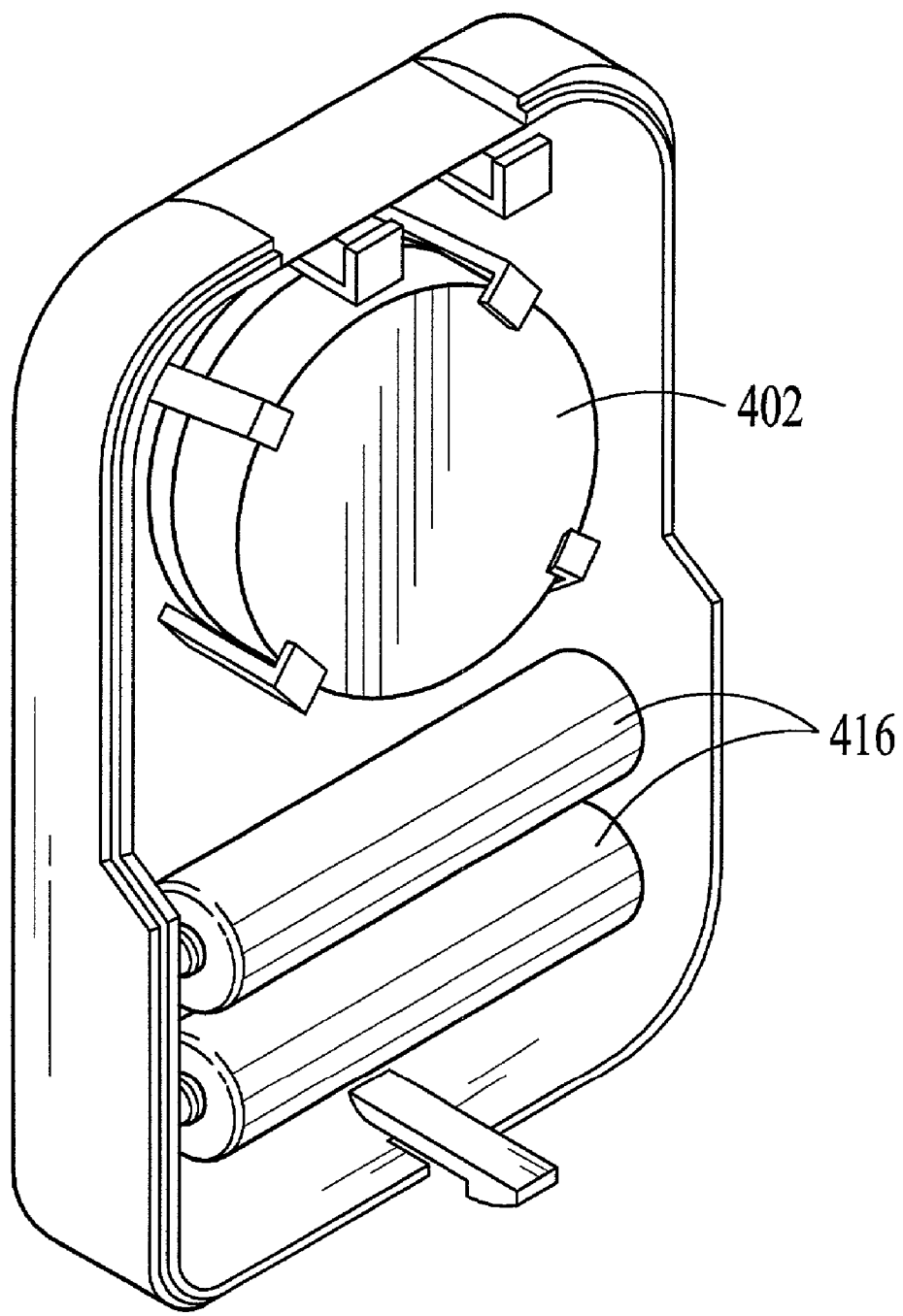
FIG. 4C is a representative isometric view of a preferred embodiment of a replacement cartridge portion of a portable emanator device of the present invention.

FIG. 4A is a representative isometric view of a preferred embodiment of a lower portion of a portable emanator device 400 of the present invention. FIG. 4B is a representative isometric view of a preferred embodiment 400 of an upper portion of a portable emanator device of the present invention. FIG. 4C is a representative isometric view of a preferred embodiment of a replacement cartridge portion 440 of a portable emanator device 400 of the present invention. As in the above embodiments of the present invention, the drawings show and describe particular designs of the portable emanator devices of the present invention. Therefore, the scope of the present invention includes these and any modified designs thereof.

In this embodiment of the personal emanator device 400, the housing has both a lower portion 420 and an upper portion 422. Vent portions allow emanating droplets to be released into the atmosphere. A control switch or panel 414 may optionally be mounted on the exterior of the device 400. The replacement cartridge portion 440 comprises a battery pack or other power source 416 as well as a liquid reservoir portion 402. As in the prior embodiments, the bubble jet portion (not entirely shown) is contained within the housing portions 420 and 422.

Figure 5:
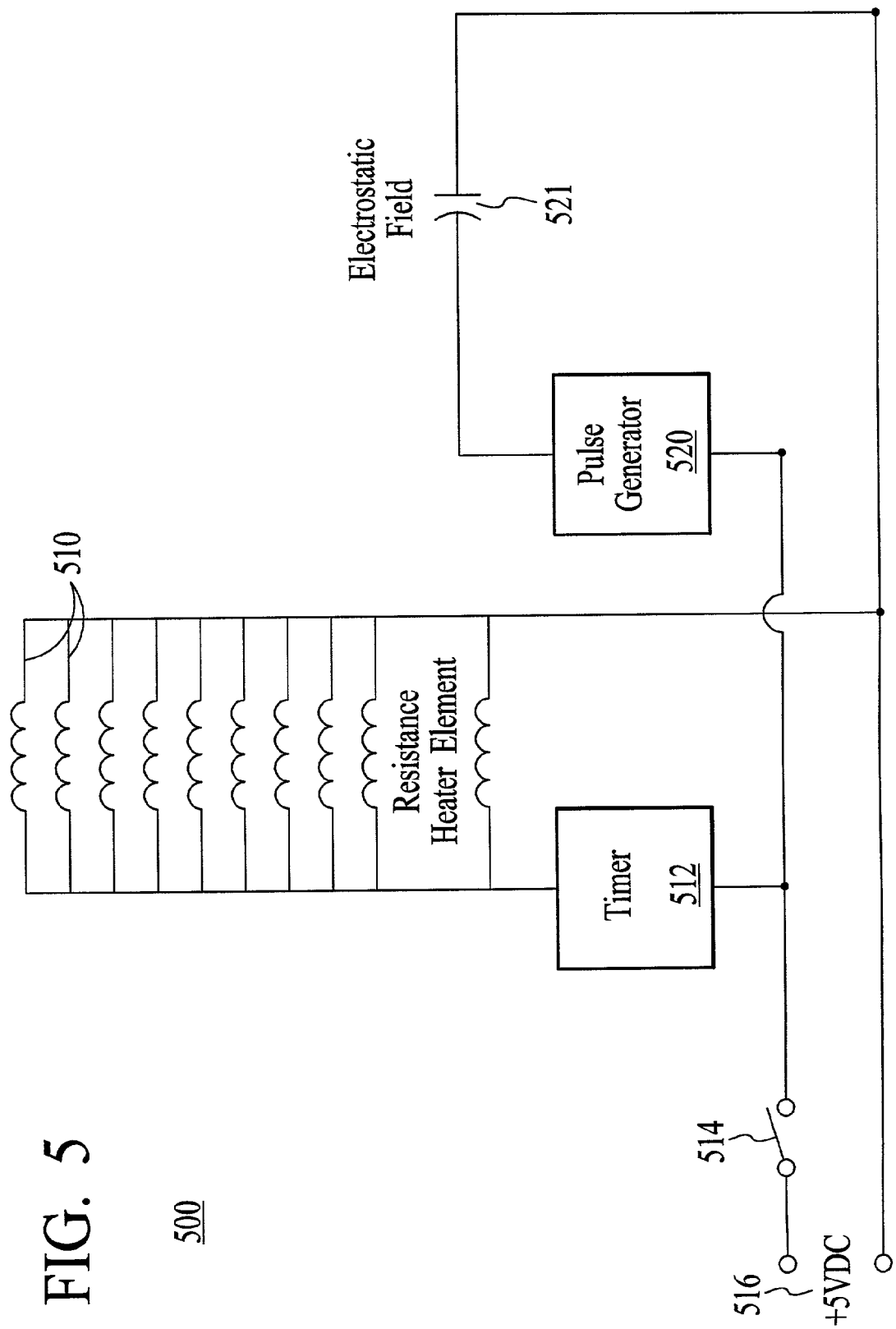
FIG. 5 is a representative electrical schematic of a preferred embodiment of the portable emanator device of the present invention.

FIG. 5 is a representative electrical schematic 500 of a preferred embodiment of the portable emanator device of the present invention. In the schematic 500, power source 516 is shown diagrammatically as a 5 volt DC battery or similar. The power source is coupled to the circuit via switch 514 or other control panel means. A timer element 512 or other control means controls the flow of power to the plurality of resistance heater elements 510 which are each associated with an independent bubble jet tube (not shown).

Coupled to the circuit in parallel, or optionally in series, is a pulse generator means 520 for developing a static field 521. As described above imparting an appropriate static charge to a droplet of insecticidal liquid 204 will enhance the attractivity of the droplets to any insects flying in the zone of protection of the device.

Other elements can be added to the circuit 500 of FIG. 5, including additional controllers, signal processors or conditioners, filters, etc. Circuit elements for stepping up or down power and signal currents and/or voltages may be employed. Energy savings elements, including timers, charging circuits, etc., can be in implemented in preferred embodiments.

Controllers can be implemented which allow a user to regulate the delivery rate, the times of delivery, the modes of delivery, etc. Timers can fire individual bubble jet tubes (as shown best in FIGS. 2A and 3A) individually, in a random or predetermined sequence, or simultaneously, etc. Lights or other visible or audible alarms which indicate on-off or any of pre-set modes of operation can be implement by those skilled in the art.

EXAMPLE 1

The ink from a Canon bubble-jet printing head has been exchanged for an insecticidal liquid 204 of the following composition:

| | |
|---|---|
| ETOC-TG | 2% |
| BHT | 4% |
| Fragrance | 0.2% |
| Ethanol | 67% |
| ISOPAR G | 26.8% |

Making up 10 mL of total solution 204. The solution 204 will last through 45 days of use assuming that the unit is left on for 11 hours each day.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method of metered delivery of an insecticidal liquid comprising the following steps:
    conmmunicating insecticidal liquid from the reservoir of a bubble-jet liquid emanator device into a capillary tube portion thereof;
    controlling the temperature of vaporization of the insecticidal liquid at a temperature at least 30° C. below the decomposition temperature of the insecticide therein;
    vaporizing a portion of the liquid within the capillary tube portion; and
    ejecting small droplets of the liquid from the bubble-jet liquid emanator device, the droplets having a volume medium diameter of between about 1 μm and about 7 μm; and
    imparting the droplets of insecticidal liquid with a static charge.

2. The method of claim 1 further comprising the step Of activating an electronic circuit containing a resistive heating element coupled to the capillary tube portion to cause an essentially instantaneous, temporary increase in temperature of the capillary tube portion.

3. The method of claim 1 further comprising the step of controlling the static charge at about $-1 \times 10_4 C/kg$.

4. The method of claim 1 further comprising the step of dissolving a suitable gas in the insecticidal liquid prior to vaporization thereof.

5. The method of claim 4 in which the gas is selected from one or more of the following hydrogen, nitrogen, oxygen, air, helium, neon, argon, krypton, xenon, methane, ethane, ethylene, acetylene, $N_2$, $CO_2$, and $O_2$.

* * * * *